United States Patent [19]

Rizzo et al.

[11] 4,228,399
[45] Oct. 14, 1980

[54] OFFSHORE PIPELINE ELECTRICAL SURVEY METHOD AND APPARATUS

[75] Inventors: Frank E. Rizzo, Spring; Marvin L. Miller; Clark Weldon, both of Houston, all of Tex.

[73] Assignee: Harco Corporation, Medina, Ohio

[21] Appl. No.: 881,737

[22] Filed: Feb. 27, 1978

[51] Int. Cl.³ .................. G01V 3/15; G01N 27/26; G01R 31/00
[52] U.S. Cl. .................................. 324/425; 324/52; 324/54; 324/65 CR; 324/71 R; 324/365
[58] Field of Search .................. 324/1, 3, 9, 52, 54, 324/67, 72, 71 R, 65 P, 65 CR, 29, 365, 347, 348

[56] References Cited

U.S. PATENT DOCUMENTS

| | | | |
|---|---|---|---|
| 2,105,247 | 1/1938 | Jakosky | 324/1 |
| 2,378,440 | 6/1945 | Scott | 324/9 X |
| 2,531,088 | 11/1950 | Thompson | 324/1 |
| 2,872,638 | 2/1959 | Jones | 324/9 X |
| 2,974,276 | 3/1961 | Davis | 324/9 X |
| 2,988,691 | 6/1961 | McAlister et al. | 324/1 |
| 3,361,957 | 1/1968 | Hings | 324/9 X |
| 3,526,831 | 9/1970 | Smith | 324/52 X |
| 3,735,249 | 5/1973 | Stoll | 324/9 |
| 4,078,510 | 3/1978 | Morgan | 324/52 X |
| 4,151,458 | 4/1979 | Seager | 324/9 |

FOREIGN PATENT DOCUMENTS

| | | | |
|---|---|---|---|
| 188676 | 12/1922 | United Kingdom | 324/3 |
| 934098 | 8/1963 | United Kingdom | 324/52 |

Primary Examiner—Gerard R. Strecker
Attorney, Agent, or Firm—Maky, Renner, Otto & Boisselle

[57] ABSTRACT

A method and apparatus for conducting offshore pipeline electrical surveys is characterized by initially locating and marking the pipeline, traversing the length of the pipeline towing a reference electrode in close proximity to the structure, providing a supply of wire having one end electrically and mechanically connected to the pipeline at a reference location, playing out the wire along the length of the pipeline through a distance measuring device while transporting the supply of wire and towing the reference electrode, and measuring and recording the potential difference between the reference electrode and pipe either continuously or at spaced test locations along the length of the structure. The method and apparatus are further characterized by alternately connecting and disconnecting an electrical power source to the pipeline at the reference location, measuring and recording the potential difference in both connected and disconnected modes at the test locations, and measuring and recording the depolarization and/or polarization times when the power source is disconnected and/or connected, respectively, to the pipeline.

21 Claims, 4 Drawing Figures

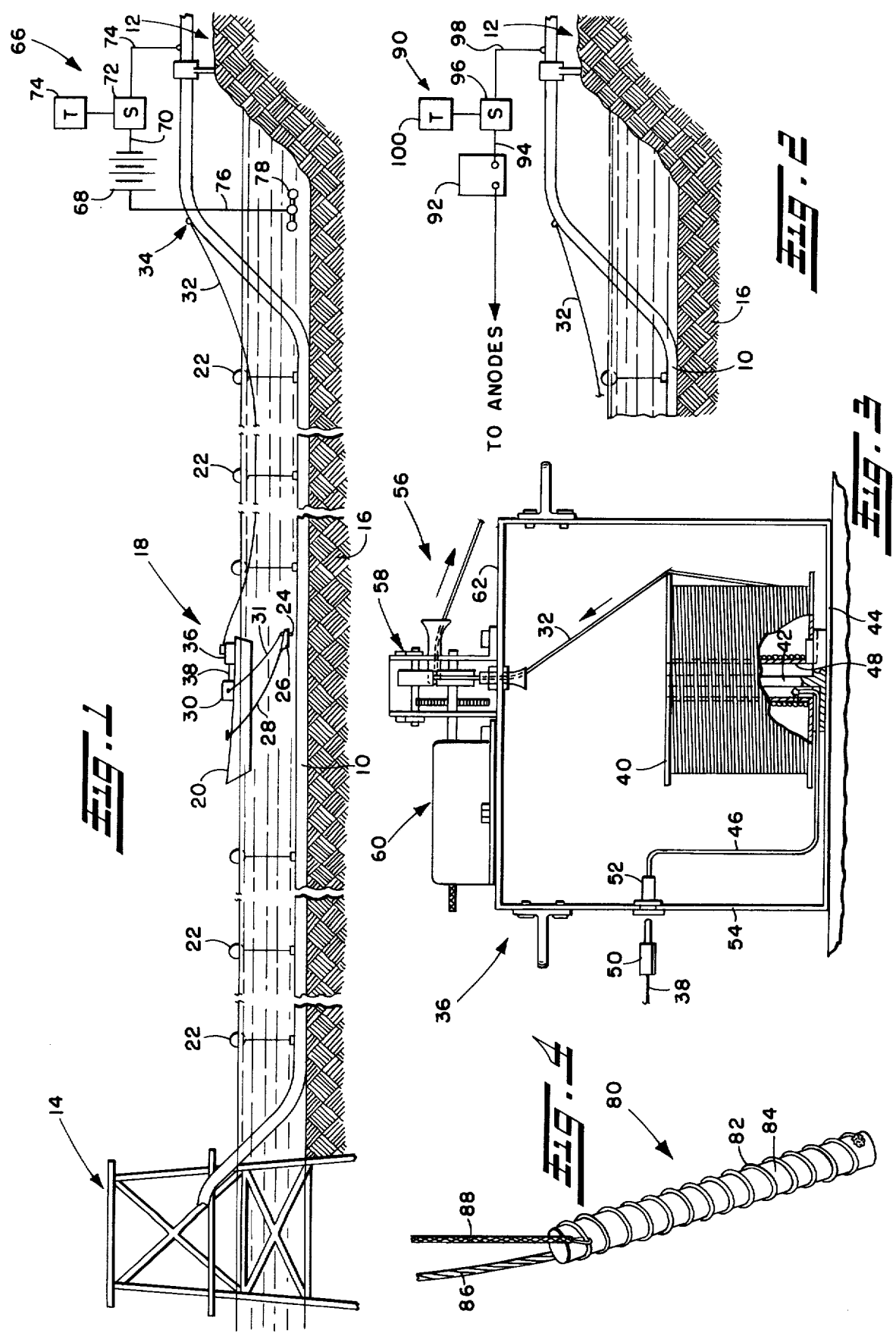

OFFSHORE PIPELINE ELECTRICAL SURVEY METHOD AND APPARATUS

BACKGROUND OF THE INVENTION

The present invention relates generally as indicated to offshore electronic surveys for marine pipelines, and more particularly to a method and apparatus for making closely-spaced electrical survey measurements for marine pipelines and the like.

Pipelines or other elongate structures in marine environments are normally installed with some form of cathodic protection system to prevent premature corrosion failures of the pipelines. An electrical current is usually passed through the water from anodes placed adjacent to a specially coated pipeline along the length thereof to reduce the potential difference between the environment and pipeline to a minimum negative potential difference. Two basic systems are employed. In galvanic protection systems, sacrificial anodes are placed in close proximity to the pipeline at spaced intervals along the length thereof. Such anodes are self-energized and are usually connected directly to the pipeline to be protected. The other basic system, commonly referred to as impressed current type, employs anodes energized by a direct current power supply such as a rectifier. The anodes are connected directly to the positive terminal of the rectifier, with the pipe or structure being protected connected to the negative terminal.

Failure of cathodic protection systems in a marine environment may occur due to inadequate design, coating damage, anode passivation, premature anode depletion, inadequate current distribution and improper anode placement. Underwater pipelines also may shift causing or aggravating the above problems. Repair of the cathodic protection system is possible, but such repair should be made before irreperable damage occurs to the structure or pipeline, as otherwise, more expensive repairs of the pipeline will be necessitated. To maintain reliability and insure optimum efficiency of the cathodic protection system, evaluations through electrical measurements are required to detect damage to the system so that necessary repairs can be made.

Such electrical corrosion measurements may be made by placing a reference electrode, such as a silver-silver chloride half cell, proximate the pipeline and measuring the potential difference between the reference electrode and pipeline. Since these electrical measurements require a contact to the pipeline, heretofore, such measurements were made on shore or on offshore platforms where the pipeline is readily accessible. In addition, very costly diver assisted measurements have been made at sub-sea valves or at relatively far apart test stations. Accordingly, areas of substantial corrosion damage may go undetected leading to premature failure of the pipeline.

SUMMARY OF THE INVENTION

The survey method of the present invention provides for intially locating the marine pipeline and marking the same between reference locations which may be, for example, on shore or on offshore platforms. An economically disposable, relatively lightweight, flexible wire is provided for electrical connection to the pipeline at a reference location and for accurate distance measurement along the length of the pipeline. The wire is wound on a reel carried by a boat and is played out behind the boat as the boat traverses the previously charted or marked pipeline. As the wire is played out, it drives a distance measuring unit also carried by the boat for measuring the distance from the reference location and between each test location. A silver-silver chloride half cell or the like is towed behind the boat and is weighted to pass proximate the pipeline. Potential measurements between the wire and the half cell are made with a suitable meter also carried by the boat. On galvanic anode protection systems a temporary impressed current system is installed, and a test current is applied to the pipeline at the referenced location and is continually pulsed. On impressed current type systems, the existing rectifier is continually pulsed. Potential measurements are taken in both on and off modes and recorded. In addition, depolarization and/or polarization times are measured by suitable means at periodic intervals along the pipeline. The recorded data is subsequently interpreted to provide an indication of the level of cathodic protection along the pipeline and identification of problem areas such as substantial coating damage and unusual current requirements.

The apparatus for conducting the survey of the present invention comprises a weighted silver-silver chloride half cell or other suitable reference electrode which is towed behind a boat as the same traverses the previously charted or marked pipeline and which is passed proximate the pipeline. Economically disposable, relatively lightweight, flexible wire is carried by a specially conductive spool and is run through a distance measuring unit carried by the boat. The wire has one end electrically connected to the pipeline at a reference location. The distance measuring unit is driven by the wire as it is played out along the pipeline, whereby accurate distance measurements may be obtained at the test end of the wire. A suitable meter is provided at the test end of the wire to measure the potential difference between the pipe and reference electrode.

The apparatus further comprises a test current source adapted to be alternately electrically connected to and disconnected from the pipeline at the reference location for applying a pulsed test current to the pipeline. The test current source is pulsed at intervals for taking and recording of potential measurements in both on and off modes and for measuring and recording depolarization and/or polarization times. For pipelines having galvanic cathodic protection systems, the test current source preferably includes a temporary ground which is electrically connected to a power source which in turn is electrically connected to the pipe via a timer or manually operated switch. Such temporary ground preferably consists of a platinumized niobium wire wrapped around a plastic tube which is adapted to be suspended in the water at the reference location. For pipelines having impressed current cathodic protection systems, the test current source comprises a power source which is electrically connected at its positive terminal to the non-sacrificial anodes of the protection system and at its negative terminal to the pipeline via a timer or manually operated switch.

It is accordingly a principal object of this invention to provide an efficient and inexpensive method and apparatus for conducting closely-spaced electrical surveys of marine pipelines or the like.

It is another important object of this invention to provide such a method and apparatus for evaluating cathodic protection systems employed with marine pipelines or the like for proper operation by identifying and locating common problems associated with such systems.

It is also an object of this invention to use in such apparatus a highly simplified light weight disposable magnet wire by which both distance and electrical measurements may be obtained.

These and other objects of the present invention may be achieved by the survey method and apparatus of the present invention.

To the accomplishment of the foregoing and related ends the invention, then, comprises the features hereinafter fully described and particularly pointed out in the claims, the following description and the annexed drawing setting forth in detail certain illustrative embodiments of the invention, these being indicative, however, of but a few of the various ways in which the principles of the invention may be employed.

BRIEF DESCRIPTION OF THE DRAWING

In the annexed drawing:

FIG. 1 is a broken schematic view illustrating the survey method of the present invention and preferred apparatus for practicing the same with marine pipelines having a galvanic cathodic protection system;

FIG. 2 is a partial schematic view of the pipeline near the shore illustrating a test current source for applying a pulsed test current to marine pipelines having an impressed current cathodic protection system;

FIG. 3 is a partially broken longitudinal elevation of the distance measuring unit of the apparatus; and FIG. 4 is a perspective view of a preferred temporary ground of the present invention.

DESCRIPTION OF THE PREFERRED EMBODIMENTS

Referring now in greater detail to the drawing, there is illustrated in FIG. 1 a typical marine pipeline 10 or other elongate structure which may be provided with one of the various types of cathodic protection systems (not shown). The pipeline 10, for example, may extend from the shore 12 to an offshore platform 14. Normally, such pipeline 10 rests on the seabed 16 or is partially buried from 2-10 feet therein, with the ends of the pipeline extending above the surface of the water near the shore 12 and offshore platform 14.

The apparatus for practicing the method of the present invention for making closely spaced electrical surveys is designated generally at 18. As shown, a boat 20 or similar vessel is shown traversing the pipeline 10 which had been previously located and marked by buoys 22 in a manner to be described. A reference electrode 24, such as a conventional silver-silver chloride half cell, is weighted to pass proximate the pipeline 10, ideally just above the pipeline or mud/water interface above the pipeline in those instances where the pipeline is buried. Preferably, the reference electrode 24 is carried in a weighted water sled 26 or the like which is towed behind the boat 20 by tow line 28. A meter 30, preferably a high input resistance type voltmeter, is carried by the boat 20 and electrically connected by lead wire 31 to the reference electrode 24 to measure the potential difference between the pipeline 10 and reference electrode 24.

The necessary electrical connection to the pipeline 10 is provided by an elongate electrical conductor 32 or wire which is electrically connected to the pipeline 10 at a reference location 34, on shore 12 as shown or on the platform 14 where the pipeline 10 is easily accessible and the electrical connection can be conveniently made. Intermediate reference locations may also be provided. The wire 32 is preferably stored in a distance measuring unit 36, carried on the boat 20, from which it is played out behind the boat as it traverses the length of the pipeline 10. Electrical connection with the other terminal of the meter 30 is provided via lead wire 38 to the distance measuring unit 36 which in turn is connected to the wire 32 as described below. Accordingly, an indication of the potential difference between the pipeline 10 and reference electrode 24 may be readily obtained by the above described apparatus 18.

As shown in FIG. 3, the wire 32 is preferably stored on a spool 40 which is supported on spindle 42 mounted at the base 44 of the distance measuring unit 36. Electrical connection of the wire 32 to the meter lead wire 38 may be provided by lead wire 46. The lead wire 46 is electrically connected to the wire 32, for example, by securing the wire 46 to the end of the wire 32 which may extend through an opening in the core 48 of the spool 40. To provide for easily electrically disconnecting the meter from the distance measuring unit, a phono type plug 50 and socket 52 mounted in one of the side walls 54 of the unit 36 may be provided.

The connecting wire 32 is sufficiently flexible for driving a distance unit counter or measuring assembly 56 as the wire is played out from the unit 36. The distance counter assembly 56 comprises a transmission assembly 58 and counter mechanism 60 driven thereby secured to the top 62 of the unit for indicating the length of wire played out from the unit. For a more detailed description of the wire length measuring assembly 56, reference may be had to applicants' assignee's copending application entitled "Closely Spaced Pipe-to-Soil Method and Apparatus," Ser. No. 820,379, filed July 29, 1977. In contrast to the unit disclosed in such application, the unit of this invention preferably is adapted to accommodate much larger spools having greater lengths of wire wound thereon.

A preferred type of connecting wire 32 is enameled copper magnet wire, such as preferably #22 to #36 A.W.G. Such wire is economically disposable and will ultimately disintegrate in the water causing no environmental harm. After completion of the survey, the wire may be left and need not be re-reeled for reuse. Of course, the wire can be retrieved for scrap.

It will be appreciated that minimal distance error will result from the wire 32 sinking in the water as it is played out behind the boat 20. Such minimal distance error can readily be taken into account. Moreover, the wire may be secured to the marker buoys 22 provided to mark the location of the pipeline 10 as will be subsequently described in connection with the method of the present invention.

As thus far described, there may be obtained an indication of the level of cathodic protection at closely spaced or essentially continuous test locations along the pipeline 10. The indicated level of protection by the meter 30, i.e., the potential difference between the reference electrode 24 and the pipeline 10, requires correction for wire and pipeline resistance errors to determine accurately the potential difference between the pipeline 10 and surrounding water. Such correction, as well as identification of areas of substantial coating damage and unusual current requirements may be obtained by applying a pulsed test current to the pipeling 10.

A preferred test current source for use with pipelines equipped with galvanic cathodic protection systems is designated generally by reference numeral 66 in FIG. 1. The test current source 66 includes an electrical power source 68, such as a lead cell battery, coupled at its negative terminal by lead wire 70 to a switch 72 which in turn is electrically coupled to the pipeline 10 by lead wire 74. Such electrical connection is provided at or close to the reference location 34 where the pipeline 10 is readily accessible. The switch 72 is operated by timer 74, or manually, alternately electrically to connect and disconnect the power source 68 with the pipeline 10 to provide the pulsed test current. The positive terminal of the power source is connected by lead wire 76 to a grounding element 78 suspended in the water to form a temporary ground bed.

A preferred temporary grounding element is shown at 80 in FIG. 4 and consists of a platinumized niobium wire 82 wrapped around a plastic tube 84. The plastic tube 84 is adapted to be suspended in the water on rope 86 and the necessary electrical connection may be provided by lead wire 88 to the power source 68. It will also be appreciated that other types of grounds may be utilized such as an aluminum rod or other conducting element suspended in the water.

A preferred test current source for use with pipelines equipped with impressed current cathodic protection systems is designated generally by reference numeral 90 in FIG. 2. The test current source 90 includes an electrical power source 92, such as a rectifier, coupled at its negative terminal by lead wire 94 to a switch 96 which in turn is electrically coupled to the pipeline 10 by lead wire 98. Such electrical connection is provided at or close to the reference location 34 where the pipeline 10 is readily accessible. The switch 96 is operated by timer 100 alternately electrically to connect and disconnect the power source 90 to the pipeline 10 to provide the pulsed test current. The positive terminal of the power source 92 is connected to the anodes of the cathodic protection system as indicated.

Typically, the test current is applied to the pipeline 10 to provide pulsed current in the following manner: 10-100 seconds off and 1-3 seconds on. Data is measured and recorded at closely-spaced intervals as the boat 20 traverses the pipeline 10 to provide for corrected pipeline-to-environment potential. In addition, depolarization and polarization times are measured and recorded to identify areas of unusual current requirement. Finally, abnormal differences between on and off potential readings at adjacent test locations will indicate areas of substantial coating damage.

It can now be seen that a closely-spaced electrical survey may be readily conducted in accordance with the present invention by utilizing the above-described apparatus. Initially, the pipeline 10 is accurately located by any one of several known techniques so that the reference electrode 24 may be passed proximate the pipeline 10 as it is towed along the length of the pipeline.

One such technique employs the use of a magnetometer for locating submerged and buried pipelines. The magnetometer is a device trailed behind a boat sensing changes in the earth's magnetic field caused by the presence of metal such as steel. The pipeline is located by making a series of "S" turns over the approximate location of the pipeline and dropping the buoys 22 where the presence of large masses of steel are indicated. Original "as-built" drawings will be helpful in approximately locating the pipeline. Marking the pipeline at 1000 foot intervals has been found adequate for straight pipeline. Much shorter intervals should be used if frequent changes in pipeline direction occur. Under optimum conditions, it has been found that about 10 miles of pipeline can be marked in an average day's work.

Another technique employing a side-scan sonar device is optimal for location of pipelines not jetted below the mud. The side-scan sonar device depicts bottom features by reflection of sonic energy from the surfaces, and provides a two-dimensional image of the bottom. "S" turning to locate the pipeline is not required with the side-scan sonar device and therefore much faster rates are possible. Under optimum conditions, 30 or more miles per day of pipeline can be marked with such device.

In those areas where there are a plurality of pipes, high-powered RF locating equipment may be employed. An RF signal is impressed in the pipeline 10 at a convenient point on shore 12 or on the offshore platform 14. A loop receiver is trailed over the suspected area to detect signal leakage. With use of such equipment, it is possible to distinguish the subject pipeline from a foreign pipeline as only the subject pipeline will carry the RF signal.

Having located and marked the pipeline 10, the boat 20 can now traverse the pipeline 10 towing the reference electrode 24. Accurate depth measurements of the seabed, and thus the pipeline, may be obtained by sonar and the reference electrode may be maintained at the measured depth by using pressure sensors secured to the sled 26. It will be appreciated that the pipeline can first be located in an initial pass and the measurements made in a second pass. Alternatively, two boats may be used with the first or lead boat locating the pipeline with the second or test boat following behind.

To begin the data run, one end of the connecting wire 32 is secured to the pipeline 10 at the reference location 34. Accordingly, mechanical and electrical connection is provided simultaneously to the pipeline 10. The timer 74 or 100 is then activated to provide a pulsed test current to the pipeline in the before described manner. The boat then traverses the length of the pipeline 10 towing the reference electrode 24 along the pipeline in close proximity thereto. The potential difference measurements in both on and off positions, and the depolarization and/or polarization times may be measured and recorded at closely spaced test locations. In the event that wire 32 on one spool 40 is exhausted, a new spool may be provided as required. Preferably, the boat carries a plurality of spools of wire, and the wire carried thereby may preferably be readily interconnected.

When the boat 20 reaches the platform 14, for example, the survey is completed and the wire 32 is left in place and never need be reeled back for reuse. In the event the pipeline 10 extends beyond the platform 14, such as to a second platform, the wire 32 may be secured to the pipeline at the platform 14 which becomes a new reference location and the survey continues as previously described from in this new reference location. The wire between the platform and the first reference location is left in place and not recovered.

The obtained data can be interpreted to provide an indication of the level of cathodic protection at each test location along the pipeline and identification of areas of substantial coating damage and unusual current requirement.

It should now be appreciated that the above method and apparatus provide for an electronic survey for marine pipelines.

The embodiments of the invention in which an exclusive property or privilege is claimed are defined as follows:

1. An apparatus for making offshore structure electrical surveys comprising reference electrode means in the environment proximate the structure, transport means to carry said reference electrode means along the length of the structure in close proximity to the structure, said transport means including a boat and said reference electrode means being towed behind said boat, a supply of flexible, small gauge, disposable elongate electrically conductive insulated magnet wire means carried by said boat for electrically and mechanically connecting the apparatus with the structure at a reference location thereon, meter means electrically connected to said wire means and electrode means for indicating the potential difference between said reference electrode means and said electrically conductive magnet wire means, and means driven by said electrically conductive magnet wire means for measuring the length of said electrically conductive magnet wire means as it is played out from the apparatus as it is carried by said transport means whereby the structure-to-environment potential difference may be determined at measured distances along the length of the structure.

2. The apparatus of claim 1 wherein said flexible elongate electrically conductive magnet wire means comprises copper magnet wire.

3. The apparatus of claim 1 wherein said flexible elongate electrically conductive magnet wire means comprises enamel insulated copper magnet wire.

4. The apparatus of claim 1 wherein said reference electrode means comprises a silver-silver chloride half cell.

5. The apparatus of claim 1 wherein said meter means and means for measuring are carried by said boat.

6. The apparatus of claim 1 further comprising means for applying a pulsed test current to the structure at such reference location.

7. The apparatus of claim 6 wherein said means for applying a pulsed test current comprises an electrical power source and switch means for alternately electrically connecting and disconnecting said power source to the structure.

8. The apparatus of claim 7 further comprising means for measuring the depolarization time when test current is switched off.

9. The apparatus of claim 7 further comprising means for measuring the polarization time when the test current is switched on.

10. The apparatus of claim 1 wherein said flexible conductive magnet wire means is disposable copper magnet wire in a size range of from about No. 22 to about No. 36 A.W.G.

11. A method for making offshore structure electrical surveys comprising the steps of:
(a) initially locating the structure to be surveyed,
(b) traversing the length of the previously located structure towing behind a boat a reference electrode in close proximity to the structure,
(c) carrying on the boat a supply of, small gauge, disposable elongate electrical insulated magnet wire conductor,
(d) electrically connecting the conductor to the structure at a reference location,
(e) playing out the conductor from the boat along the length of the structure while transporting the supply of the conductor and towing the reference electrode behind the boat,
(f) measuring and recording the potential difference between the reference electrode and conductor at spaced test locations along the length of the structure, and
(g) determining the position of such test locations relative to the pipe.

12. The method of claim 11 wherein such test locations are at closely spaced regular intervals along the structure and the location of said test locations relative to the structure determined by playing out the conductor through a distance measuring device.

13. The method of claims 11 or 12 wherein the flexible elongate electrical insulated magnet wire conductor is disposable copper magnet wire in a size range of from about No. 22 to about No. 36 A.W.G.

14. The method of claim 11 wherein the structure is marked by a plurality of buoys.

15. The method of claim 11 wherein a magnetometer is employed to locate the structure.

16. The method of claim 11 wherein side-scan sonar is employed to locate the structure.

17. The method of claim 11 wherein high powered RF equipment is employed to locate the structure.

18. The method of claim 11 wherein the depth of the structure is obtained by sonar and the depth of the reference electrode by pressure sensors.

19. The method of claim 11 further comprising the steps of:
(g) alternately connecting and disconnecting an electrical power source to the structure at the reference locations, and
(h) measuring and recording the potential difference in both connected and disconnected modes at such test locations.

20. The method of claim 19 further comprising the step of:
(i) measuring and recording the depolarization times when the power source is disconnected.

21. The method of claim 19 further comprising the step of:
(j) measuring and recording the polarization time when the power source is connected.

* * * * *